(12) United States Patent
Kim

(10) Patent No.: US 11,928,815 B2
(45) Date of Patent: Mar. 12, 2024

(54) METHOD AND APPARATUS FOR ANALYZING MEDICAL IMAGE

(71) Applicant: Electronics and Telecommunications Research Institute, Daejeon (KR)

(72) Inventor: Hang Kee Kim, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 403 days.

(21) Appl. No.: 17/353,071

(22) Filed: Jun. 21, 2021

(65) Prior Publication Data

US 2021/0398279 A1   Dec. 23, 2021

(51) Int. Cl.
*G06T 7/00* (2017.01)
*G06T 7/149* (2017.01)

(52) U.S. Cl.
CPC ............ *G06T 7/0012* (2013.01); *G06T 7/149* (2017.01); *G06T 2207/10116* (2013.01); *G06T 2207/30012* (2013.01)

(58) Field of Classification Search
CPC ......... G06T 7/0012; G06T 2207/10116; G06T 2207/30012
USPC ....................................................... 382/128
See application file for complete search history.

(56) References Cited

U.S. PATENT DOCUMENTS

| | | | |
|---|---|---|---|
| 6,560,474 B2 | 5/2003 | Lee et al. | |
| 9,401,020 B1* | 7/2016 | Li | G06V 20/647 |
| 2002/0133097 A1* | 9/2002 | Leitner | A61B 5/6838 |
| | | | 600/587 |
| 2011/0021914 A1 | 1/2011 | Zheng et al. | |
| 2011/0058720 A1* | 3/2011 | Lu | G06T 7/344 |
| | | | 382/128 |
| 2011/0306873 A1* | 12/2011 | Shenai | A61B 8/0841 |
| | | | 600/424 |
| 2015/0287184 A1* | 10/2015 | Parent | G06T 7/0012 |
| | | | 382/128 |
| 2017/0020626 A1 | 1/2017 | Schlenger | |
| 2017/0340268 A1 | 11/2017 | Danielsson et al. | |
| 2018/0286050 A1* | 10/2018 | Cheng | G06T 7/143 |

(Continued)

FOREIGN PATENT DOCUMENTS

| | | |
|---|---|---|
| EP | 3 417 776 | 12/2018 |
| KR | 10-1265981 | 5/2013 |
| KR | 10-1542663 | 8/2015 |

(Continued)

*Primary Examiner* — Gabriel I Garcia
(74) *Attorney, Agent, or Firm* — KILE PARK REED & HOUTTEMAN PLLC

(57) ABSTRACT

The present disclosure provides a medical image analysis method and apparatus. The medical image analysis method according to an exemplary embodiment includes: receiving a frontal image of a spine; separating vertebral bodies from a vertebrae constituting the spine in the frontal image and extracting a contour of each of the vertebral bodies; deforming a 3D vertebral body model prepared in advance to match with the contour of each vertebral body; detecting an upper plane and a lower plane of each vertebral body in a matched 3D vertebral body model; determining an inclination of each vertebral body based on the upper plane and the lower plane of each vertebral body; and calculating a Cobb's angle based on the inclination of the vertebral body.

20 Claims, 11 Drawing Sheets

(56) References Cited

U.S. PATENT DOCUMENTS

2019/0295278 A1     9/2019  Kim et al.
2021/0145519 A1*    5/2021  Mosnier ............ A61B 17/7077

FOREIGN PATENT DOCUMENTS

| KR | 10-2016-0092666 | 8/2016 |
| KR | 10-2018-0092797 | 8/2018 |
| KR | 10-1968144      | 8/2019 |

* cited by examiner

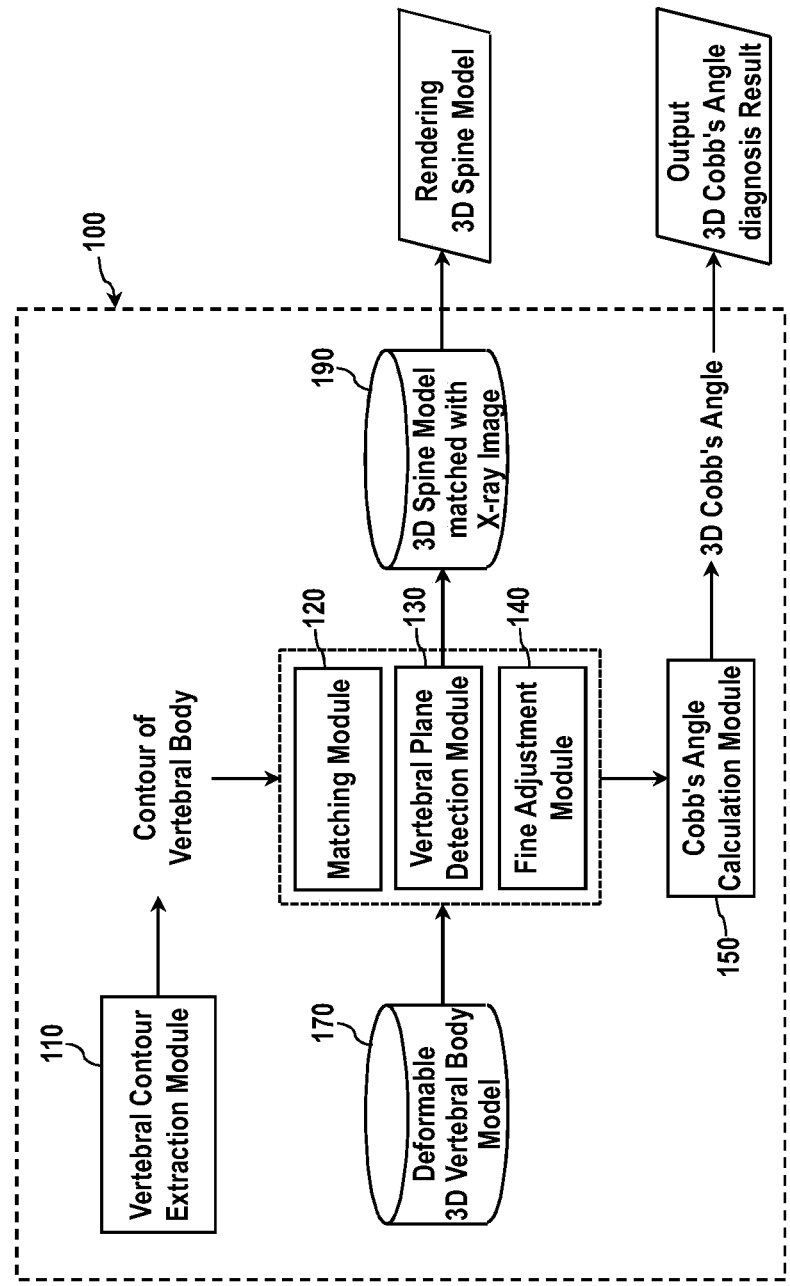

METHOD AND APPARATUS FOR ANALYZING MEDICAL IMAGE

CROSS-REFERENCE TO RELATED APPLICATION

The present application claims priority to Korean Patent Application No. 10-2020-0075785 filed on Jun. 22, 2020 with the Korean Intellectual Property Office (KIPO), the entire content of which is incorporated herein by reference.

BACKGROUND

1. Technical Field

The present disclosure relates to a medical image analysis method and apparatus and, more particularly, to a medical image analysis method and apparatus for deriving a Cobb's angle of a spine using a single frontal X-ray image.

2. Related Art

Image analysis methods for diagnosing a disease of a spine use an X-ray, computed tomography (CT), or magnetic resonance imaging (MRI) image. The spine disease analysis using the CT or MRI image generates a three-dimensional (3D) model of a shape of the spine and enables the disease analysis more accurately and precisely. However, such an analysis requires a large cost for the imaging and, especially in a case of the CT, a subject is exposed to a significant amount of radiation.

In order to solve these shortcomings, a 3D modeling using the X-ray image being inexpensive and resulting in a relatively small amount of exposure to the radiation is being used. The 3D modeling using the X-ray image generally use two or more X-ray images because the 3D modeling using just a single image allows to find the shape of the spine only in the x-axis (i.e., horizontal) and y-axis (i.e., vertical) directions but does not provide information in the z-axis (i.e., depth) direction, which results in an inaccurate 3D modeling result.

However, even when two or more X-ray images are used, it is difficult to combine the X-ray images unless the images are photographed in directions perpendicular to each other at the same time and, in particular, a problem of matching skeletal parts in the images remains a difficult problem.

Meanwhile, in one of the methods of analyzing the spinal diseases using the X-ray images, Cobb's angle is derived from the images and a size of the angle is analyzed to diagnose a spinal deformity and determine whether to perform a surgical treatment. The Cobb's angle calculated from a two-dimensional image, however, may cause an incomplete diagnosis of the spine which has a three-dimensional structure.

SUMMARY

In order to solve the above problems, provided is a medical image analysis method for deriving the Cobb's angle of the spine using a single frontal X-ray image.

Provided is a medical image analysis apparatus utilizing the medical image analysis method.

According to an aspect of an exemplary embodiment, a medical image analysis method includes: receiving a frontal image of a spine; separating vertebral bodies from a vertebrae constituting the spine in the frontal image and extracting a contour of each of the vertebral bodies; deforming a 3D vertebral body model prepared in advance to match with the contour of each vertebral body; detecting an upper plane and a lower plane of each vertebral body in a matched 3D vertebral body model; determining an inclination of each vertebral body based on the upper plane and the lower plane of each vertebral body; and calculating a Cobb's angle based on the inclination of the vertebral body.

The medical image analysis method may further include: performing a fine adjustment of the 3D vertebral body model; and recalculating the Cobb's angle based on a fine-adjusted 3D vertebral body model.

The operation of deforming the 3D vertebral body model to match with the contour of each vertebral body may include: deforming the 3D vertebral body model by changing at least one of a position, rotation, and shape of the 3D vertebral body model and matching a deformed 3D vertebral body model with the contour of each vertebral body.

The operation of deforming the 3D vertebral body model to match with the contour of each vertebral body may include: determining a forward tilt or a backward tilt of a particular vertebral body in consideration of a position of the particular vertebral body in an entire body of the spine and characteristics of the spine.

The characteristics of the spine may include a feature of thoracic kyphosis or lumbar lordosis and a continuity between adjacent vertebral bodies.

The operation of performing the fine adjustment of the 3D vertebral body model may include: setting a chain line connecting the vertebral bodies constituting the spine using inclinations of the upper and lower planes of each vertebral body; determining a reference plane with reference to the chain line; and adjusting a difference in angles between the upper plane of a corresponding vertebral body and the reference plane and between the lower plane of the corresponding vertebral body and the reference plane.

The reference plane may be a plane of which normal vector is an average of two direction vectors that are parallel with chain lines connecting to a lower adjacent vertebral body and an upper adjacent vertebral body, respectively, of a particular vertebral body.

The reference plane may be a plane bisecting an angle formed by a first chain line connecting to a lower adjacent vertebral body of a particular vertebral body and a second chain line connecting to an upper adjacent vertebral body of the particular vertebral body.

The Cobb's angle may be set as an angle between two arbitrary planes having a largest angle among the angles formed by any two of upper planes and lower planes of the vertebral bodies constituting the spine in a 3D space.

The medical image analysis method may include: providing the Cobb's angle to diagnose a spine-related disease.

The image may be a 2D X-ray image.

According to another aspect of an exemplary embodiment, a medical image analysis apparatus includes: a processor; and a memory storing at least one instruction to be executed by the processor. The at least one instruction, when executed by the processor, causes the processor to: receive a frontal image of a spine and separate vertebral bodies from a vertebrae constituting the spine in the frontal image; extract a contour of each of the vertebral bodies; deform a 3D vertebral body model prepared in advance to match with the contour of each vertebral body; detect an upper plane and a lower plane of each vertebral body in a matched 3D vertebral body model; determine an inclination of each vertebral body based on the upper plane and the lower plane of each vertebral body; and calculate a Cobb's angle based on the inclination of the vertebral body.

The at least one instruction, when executed by the processor, may further cause the processor to: perform a fine adjustment of the 3D vertebral body model; and recalculate the Cobb's angle based on a fine-adjusted 3D vertebral body model.

The instruction causing the processor to deform the 3D vertebral body model to match with the contour of each vertebral body may include instructions causing the processor to: deform the 3D vertebral body model by changing at least one of a position, rotation, and shape of the 3D vertebral body model and match a deformed 3D vertebral body model with the contour of each vertebral body.

The instruction causing the processor to deform the 3D vertebral body model to match with the contour of each vertebral body may include instructions causing the processor to: determine a forward tilt or a backward tilt of a particular vertebral body in consideration of a position of the particular vertebral body in an entire body of the spine and characteristics of the spine.

The instruction causing the processor to perform the fine adjustment of the 3D vertebral body model may include instructions causing the processor to: set a chain line connecting the vertebral bodies constituting the spine using inclinations of the upper and lower planes of each vertebral body; determine a reference plane with reference to the chain line; and adjust a difference in angles between the upper plane of a corresponding vertebral body and the reference plane and between the lower plane of the corresponding vertebral body and the reference plane.

The reference plane may be a plane of which normal vector is an average of two direction vectors that are parallel with chain lines connecting to a lower adjacent vertebral body and an upper adjacent vertebral body, respectively, of a particular vertebral body.

The Cobb's angle may be set as an angle between two arbitrary planes having a largest angle among the angles formed by any two of upper planes and lower planes of the vertebral bodies constituting the spine in a 3D space.

The at least one instruction, when executed by the processor, may further cause the processor to: provide the Cobb's angle to diagnose a spine-related disease.

The image may be a 2D X-ray image.

According to exemplary embodiments of the present disclosure, a diagnosis of a spinal disease may be performed by use of an X-ray image instead of a CT or MRI image. Furthermore, a three-dimensional spine model is constructed using only a single frontal X-ray image to facilitate the diagnosis. Thus, exemplary embodiments of the present disclosure allows to save time and cost required for the diagnosis.

In addition, exemplary embodiments of the present disclosure enables to calculate the Cobb's angle more precisely than a conventional 2D X-ray image-based calculation method, and may be applicable in a diagnosis of scoliosis and in a determination whether to proceed with a surgery.

BRIEF DESCRIPTION OF THE DRAWINGS

In order that the disclosure may be well understood, there will now be described various forms thereof, given by way of example, reference being made to the accompanying drawings, in which:

FIG. 1 is a block diagram of a medical image analysis apparatus according to an exemplary embodiment of the present disclosure;

DETAILED DESCRIPTION

Figure 2A:
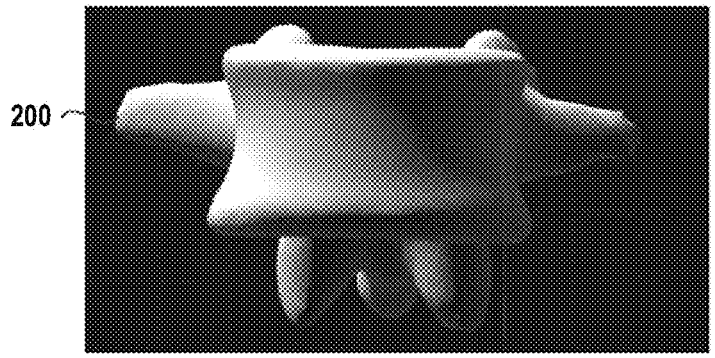
FIGS. 2A through 2C show shapes of a vertebrae and a vertebral body considered in the present disclosure.

For a more clear understanding of the features and advantages of the present disclosure, exemplary embodiments of the present disclosure will be described in detail with reference to the accompanied drawings. However, it should be understood that the present disclosure is not limited to particular embodiments disclosed herein but includes all modifications, equivalents, and alternatives falling within the spirit and scope of the present disclosure. In the drawings, similar or corresponding components may be designated by the same or similar reference numerals.

The terminologies including ordinals such as "first" and "second" designated for explaining various components in this specification are used to discriminate a component from the other ones but are not intended to be limiting to a specific component. For example, a second component may be referred to as a first component and, similarly, a first component may also be referred to as a second component without departing from the scope of the present disclosure. As used herein, the term "and/or" may include a presence of one or more of the associated listed items and any and all combinations of the listed items.

When a component is referred to as being "connected" or "coupled" to another component, the component may be directly connected or coupled logically or physically to the other component or indirectly through an object therebetween. Contrarily, when a component is referred to as being "directly connected" or "directly coupled" to another component, it is to be understood that there is no intervening object between the components. Other words used to describe the relationship between elements should be interpreted in a similar fashion.

The terminologies are used herein for the purpose of describing particular exemplary embodiments only and are not intended to limit the present disclosure. The singular forms include plural referents as well unless the context clearly dictates otherwise. Also, the expressions "comprises," "includes," "constructed," "configured" are used to refer a presence of a combination of stated features, numbers, processing steps, operations, elements, or components, but are not intended to preclude a presence or addition of another feature, number, processing step, operation, element, or component.

Unless defined otherwise, all terms used herein, including technical or scientific terms, have the same meaning as commonly understood by those of ordinary skill in the art to which the present disclosure pertains. Terms such as those defined in a commonly used dictionary should be interpreted as having meanings consistent with their meanings in the context of related literatures and will not be interpreted as having ideal or excessively formal meanings unless explicitly defined in the present application.

Exemplary embodiments of the present disclosure will now be described in detail with reference to the accompanying drawings.

FIG. 1 is a block diagram of a medical image analysis apparatus according to an exemplary embodiment of the present disclosure.

The medical image analysis apparatus 100 according to the present embodiment may include a vertebral contour extraction module 110, a matching module 120, a vertebral plane detection module 130, a fine adjustment module 140, and a Cobb's angle calculation module 150. Also, the medical image analysis apparatus 100 may further include a deformable 3D vertebral body model 170 and a 3D spine model 190 matched with X-ray image.

The medical image analysis apparatus according to the present disclosure receives a single frontal X-ray image. The vertebral contour extraction module 110 extracts each vertebrae and a contour of each vertebral body from the input X-ray image.

The matching module 120 performs a deformation of a position, direction, or shape on the 3D vertebral body model 170 prepared in advance to match with a contour of the each vertebral body extracted from the X-ray image. The 3D spine model 190 deformed to match the vertebral contour may be provided to a user through a rendering process. The vertebral plane detection module 130 detects planes corresponding to bottom and top surfaces of each vertebral body with respect to the 3D vertebral body model 190 that has been matched.

The fine adjustment module 140 forms a chain line of each vertebral body based on inclinations of normal lines for the 3D planes for the corresponding vertebral bodies and compares an angle between the chain line and the horizontal planes of each vertebral body to make a fine adjustment of the 3D vertebral body model 170. The Cobb's angle calculation module 150 calculates the 3D Cobb's angle using the finely adjusted vertebral plane to provide the calculated Cobb's angle for the diagnosis of the spinal diseases.

To summarize, the input to the medical image analysis apparatus 100 is a single frontal X-ray image including the spine, and the output of the apparatus 100 is the 3D spine model and the 3D Cobb's angle value.

In general, the 3D modeling using the X-ray image uses two or more X-ray images. This is because the 3D modeling using just a single image allows to find the shape of the spine in the x-axis (i.e., horizontal) direction and y-axis (vertical) direction but does not provide information in the z-axis (i.e., depth) direction. The present disclosure enables to estimate the 3D depth and increase the accuracy of the 3D modeling through an analysis of a single frontal image, which may be one of the differences from the other spine 3D modeling method.

Meanwhile, the 3D vertebral body model 170 stored in advance in the present disclosure is a deformable 3D vertebral body model. In case that the model is created by a statistical shape model (SSM), the vertebral body part is separated from a sample set of the vertebra model, and SSM parameters are adjusted through a principal component analysis (PCA), so that the 3D vertebral body model is deformable into one of the shapes in a sample set. In case that the 3D vertebral body model is deformable in a free form deformation (FFD) method, a standard skeletal model and a corresponding model for adjustment may include a number of grid vertices and so on.

Figure 2B:
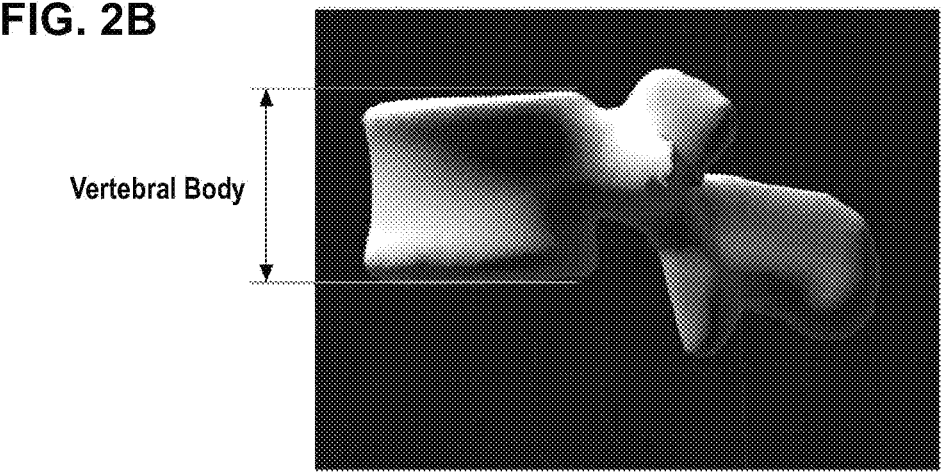
Figure 2C:
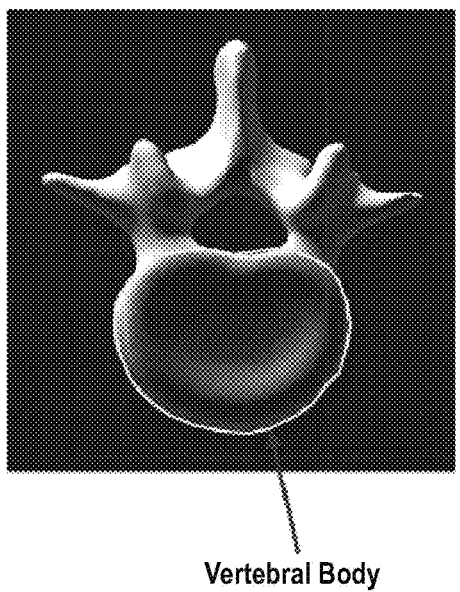

FIGS. 2A through 2C show exemplary shapes of a vertebrae and a vertebral body considered in the present disclosure.

FIG. 2A shows a shape of the vertebra 200 constituting each node of the spine. In the vertebrae 200, a portion that forms the body of the vertebra 200 excluding protrusions such as a spinous process, a transverse process, and a superior articular process and a lamina behind that vertebrae 200 is referred to as the vertebral body.

The vertebral body of each node has the shape slightly different from the other nodes, but generally has a cylindrical shape and the bottom and top surfaces of the vertebral body are generally oval-shaped planes as shown in FIGS. 2B and 2C.

Figure 3:
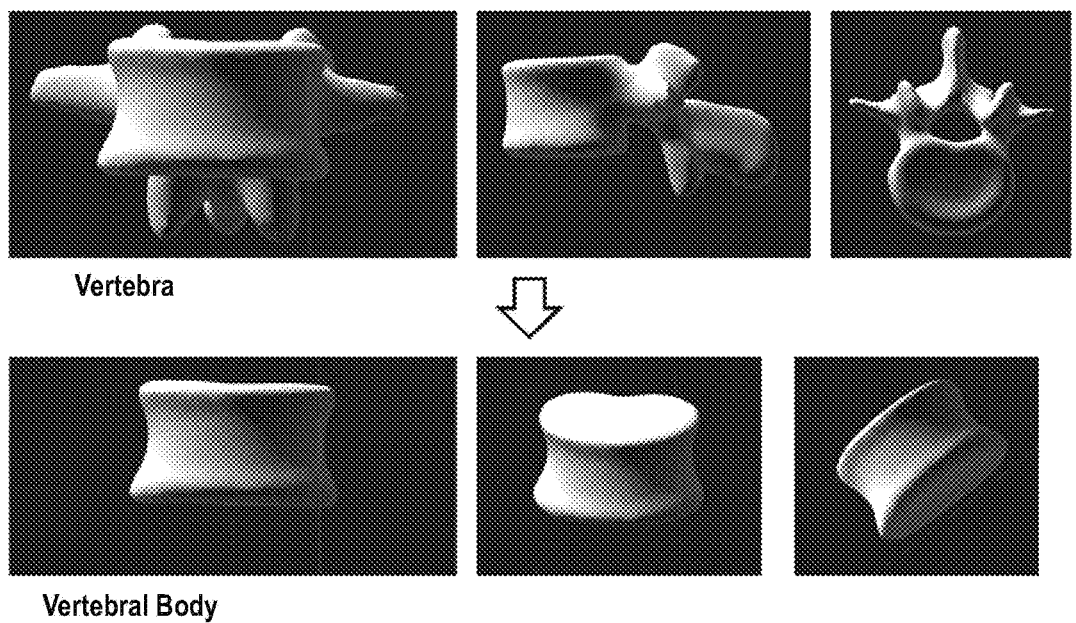
FIG. 3 illustrates a concept of separating a vertebral body portion from a vertebrae according to an exemplary embodiment of the present disclosure.

FIG. 3 illustrates a concept of separating the vertebral body portion from the vertebrae according to an exemplary embodiment of the present disclosure.

In an embodiment of the present disclosure, a 3D modeling may be performed on the vertebral body and a calculation of the Cobb's angle may be performed in the 3D vertebral body model. To this end, only the vertebral body may be separated from a 3D model for each vertebra to generate the deformable 3D vertebral body model as shown in FIG. 3

Figure 4:
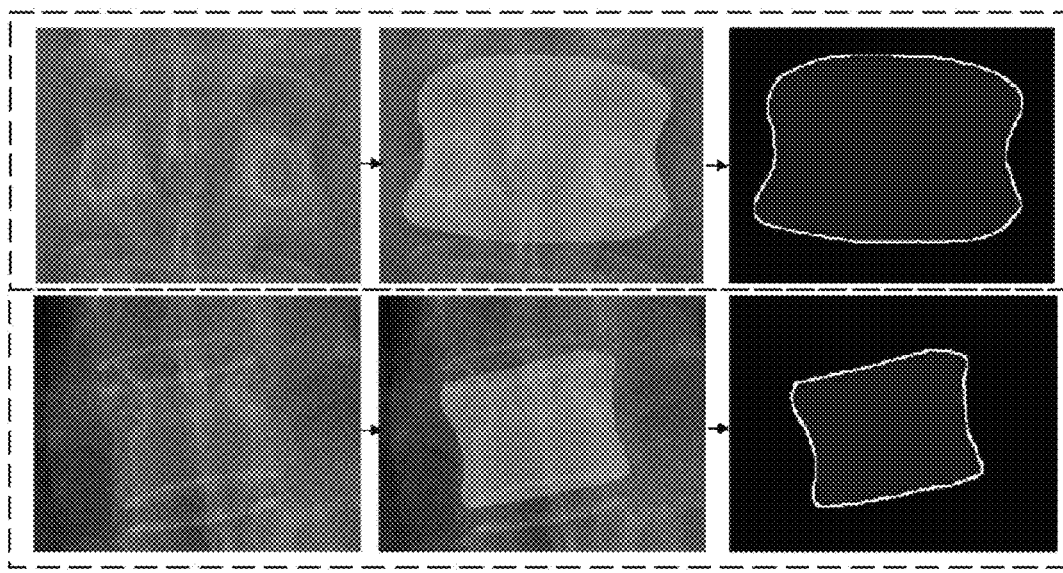
FIG. 4 illustrates a concept of setting a contour of a vertebral body in an X-ray image according to an exemplary embodiment of the present disclosure.

FIG. 4 illustrates a concept of setting the contour of the vertebral body in the X-ray image according to an exemplary embodiment of the present disclosure.

As shown in FIG. 4, the contour of the vertebral body of each vertebrae in the X-ray image can be identified relatively clearly. When the contour of the vertebral body is being set, other parts such as the processes and the lamina other than the vertebral body are not considered. A size and shape of the contour of the vertebral body are slightly different between the nodes of the spine, and may further change according to tilts in the x-axis (i.e. horizontal) direction, y-axis (vertical) direction, and z-axis (depth) direction of the vertebral body. The present disclosure calculates the 3D tilt of each vertebral body by using the difference in shape according to the tilts of the vertebral body in the x-axis, y-axis, and z-axis directions and calculates a relative depth, i.e., z value, of each vertebral body by using the 3D tilt.

Since the vertebral body has the cylindrical shape, the vertebral body has a shape close to a rectangle in the frontal view if there is no tilt in a lateral direction. However, as the tilt in the lateral direction increases, the lower and upper sides of the vertebral body appear convex in an elliptical shape. Therefore, the larger the convex curves of the bottom and top surfaces of the vertebral body, the greater the tilt in the lateral side.

The contour of the vertebral body may be set by a semantic segmentation, for example, using deep learning. Also, the contour of the vertebral body may be set by the user. Also available is a semi-automatic method in which the contour of the vertebral body is set automatically by the deep learning but contour portions that is inaccurately set may be corrected manually.

Figure 5:
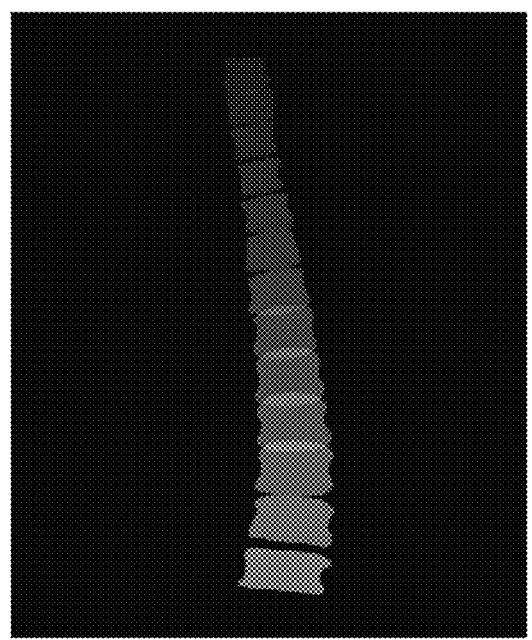
FIG. 5 shows contours of all vertebral bodies of a spine of which contours are set according to an exemplary embodiment of the present disclosure.

FIG. 5 shows contours of all the vertebral bodies of the spine of which contours are set according to an exemplary embodiment of the present disclosure.

In the present disclosure, the contour of the vertebral body is set for each vertebral node of the entire spine. As shown in FIG. 5, some portions of adjacent vertebral bodies may seem to overlap in a contour image of all the vertebral bodies set for the entire spine according to the tilt in a lateral view of the spine. However, such portions are not actual overlaps between the vertebral bodies, but are just apparent overlaps. Such apparent overlaps arise when the bottom and top surfaces of the vertebral bodies are convexly revealed in the elliptical shapes as each of the vertebrae separated from each other in the actual 3D space is tilted in the x-axis, y-axis, or z-axis direction.

Figure 6:
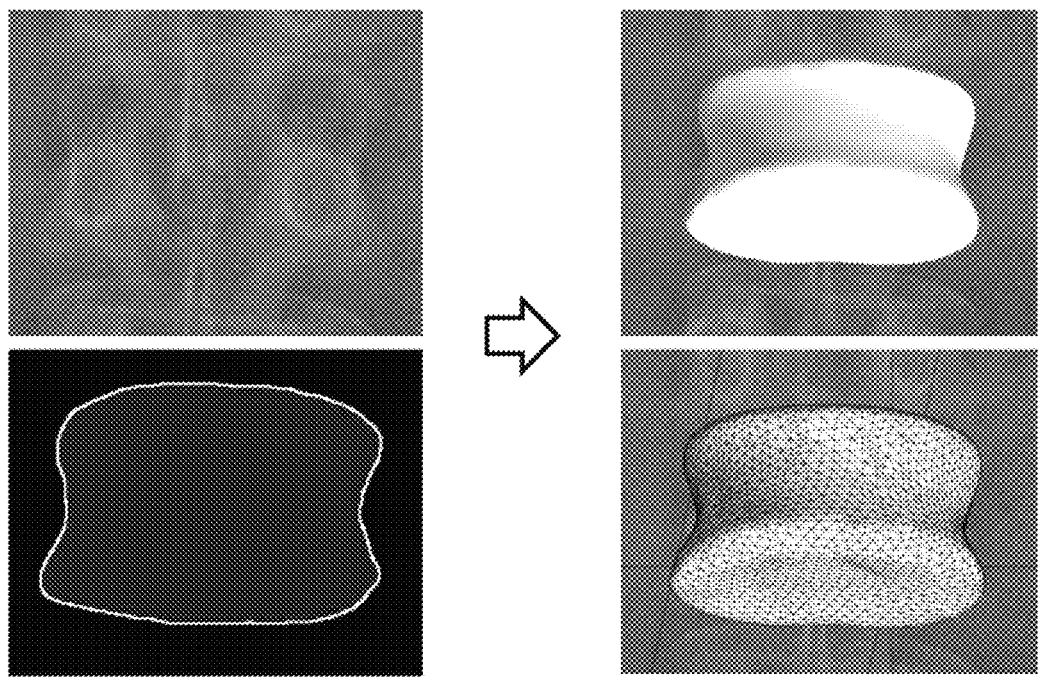
FIG. 6 illustrates a concept of matching a 3D model of a vertebral body with the contour in the X-ray image according to an exemplary embodiment of the present disclosure.

FIG. 6 illustrates a concept of matching the 3D vertebral body model with the contour in the X-ray image according to an exemplary embodiment of the present disclosure.

In the present disclosure, the 3D vertebral body model may be matched with the contour of the vertebral body derived from the X-ray image through a deformation of the position, direction, size, or shape of the 3D vertebral body model.

The 3D vertebral body model used in the present disclosure may be subject to a translation, rotation, and deformation. Thus, the 3D vertebral body model may be matched with the contour of the vertebral body set in the X-ray image by changing a position value (Tx, Ty, Tz), a rotation value (Rx, Ry, Rz), and the shape of the 3D vertebral body model. The 3D vertebral body model may be optimized by performing matching trials repetitively until the contour of the 3D vertebral body model coincides the contour of the vertebral body set in the X-ray image.

At this time, the shape of the 3D vertebral body model may be changed by the free form deformation (FFD) method or the statistical shape model (SSM) method.

The free form deformation (FFD) method divides an entire region in the image into grids and moves vertices of each grid as necessary. The statistical shape model (SSM) statistically analyzes a sample set of the 3D vertebral body model and uses parameters based on principal component analysis (PCA). In case that there are lots of samples of the vertebral body, the deformation by the SSM may deform the shape of the 3D vertebral body model closer to the actual model than the FFD.

Meanwhile, when calculating the rotation value of the vertebral body, the tilt in the frontal view can be identified immediately, but the tilt in the side view may be calculated inevitably by estimating the shape of the vertebral body.

In case that the vertebral body is tilted when viewed from the side, it may be tilted forward or backward. In both cases, however, the shapes when viewed simply from the frontal X-ray image may be the same as each other. Whether the vertebral body is tilted forward or backward can be discriminated using two clues described below.

First, although the shape of the spine may be different for each individual, there are features which are common for the mankind. That is, the human spine has a morphological characteristic of a thoracic kyphosis according to which the vertebrae of the chest area (chest areas T1~T12) bend like a humpback and a lumbar lordosis according to which the vertebrae of the waist area (L1~L5 waist) bend in the opposite direction. Accordingly, there are two vertebral bodies of which shape in the frontal X-ray have the rectangular shape without the lateral tilt, one at the thoracic region and the other one at the lower lumbar region. Based on this morphological characteristic, it can be assumed that the upper part has the shape of a lordosis that bends like the humpback lamp, and the lower part has the shape of a kyphosis that bends in the opposite direction. Therefore, if there is just a single vertebral body in the frontal X-ray which appears as a rectangle without the lateral tilt, it may be probable that the spine has little lumbar lordosis and the spine has the thoracic kyphosis.

Second, the vertebrae are connected like a chain. Thus, each vertebrae changes its direction little by little while maintaining a continuity in the direction with the lower and upper adjacent vertebrae.

Figure 7B:
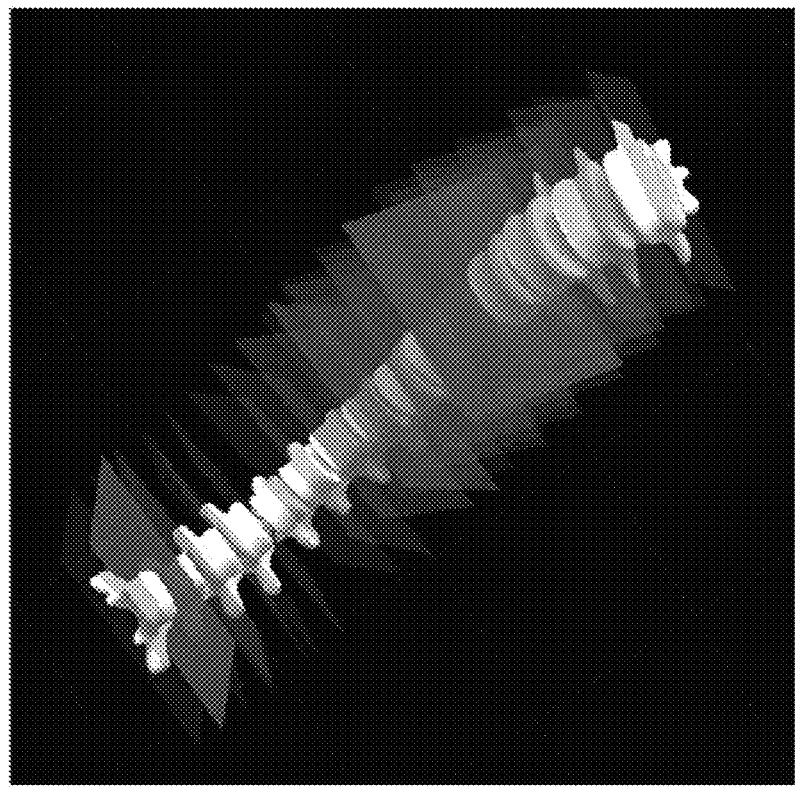
FIG. 7B illustrates a concept of detecting upper and lower planes of the vertebral body.
Figure 7A:
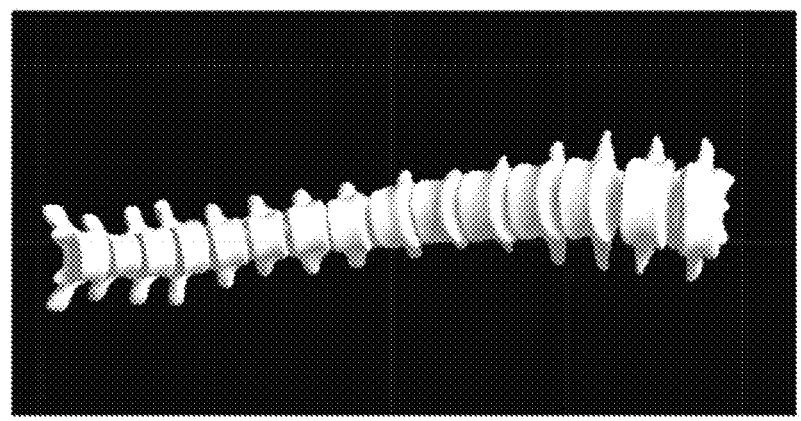
FIG. 7A illustrates a 3D modeling of the vertebral body according to an exemplary embodiment of the present disclosure.

FIG. 7A illustrates a 3D modeling of the vertebral body according to an exemplary embodiment of the present disclosure, and FIG. 7B illustrates a concept of detecting upper and lower planes of the vertebral body.

Since each the vertebral body has a cylindrical shape, top and bottom surfaces of the vertebral body can be approximated with a circular 3D plane. Such an approximation can be calculated using a sample consensus (SAC) method or an iterative closest point (ICP) method. When the lower and upper 3D planes of a cylinder are derived, the tilt of the vertebral body may be represented by a normal line of the plane. The 3D planes can be used to derive an initial value for the Cobb's angle.

According to the present disclosure, the initial value of Cobb's angle may be supplemented by a fine adjustment based on a chain line structure, which will be described in detail below.

Figure 8B:
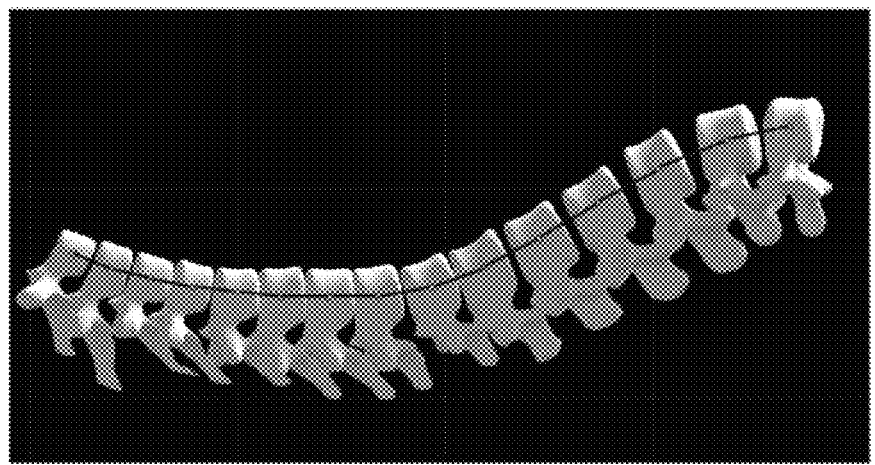
FIGS. 8A and 8B illustrate a chain line connecting 3D vertebral bodies when viewed from a front and a side, respectively.
Figure 8A:
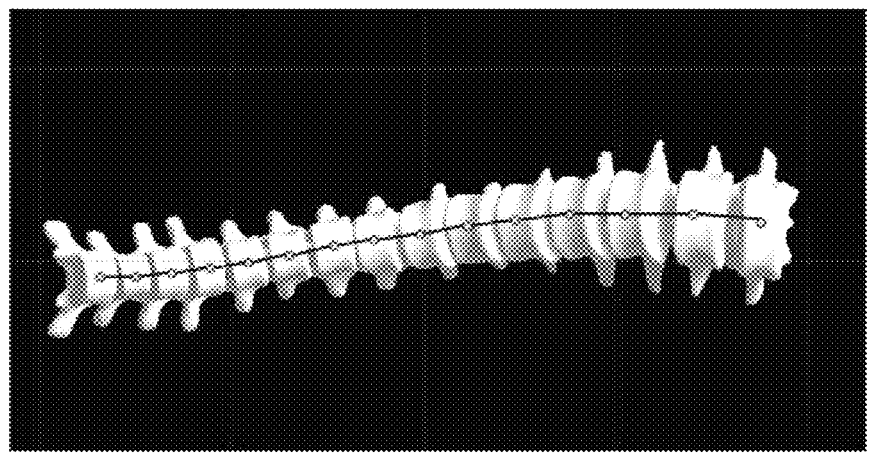

FIGS. 8A and 8B illustrate a chain line connecting the 3D vertebral bodies when viewed from a front and a side, respectively.

Referring to FIGS. 8A and 8B, the vertebrae are sequentially connected like a chain. Therefore, each vertebra has a direction similar to those of adjacent lower and upper vertebrae but changes the direction little by little from the lower and upper vertebrae. In other words, the direction of a vertebra does not change suddenly or significantly from those of the lower and upper vertebrae. In case that there is at least one vertebral bodies of which forward tilt or the rear tilt is incorrectly estimated, a change of an estimate for a single representative vertebral body can automatically correct the directions of the rest vertebral bodies according to the assumption of the chain shape.

Figure 9:
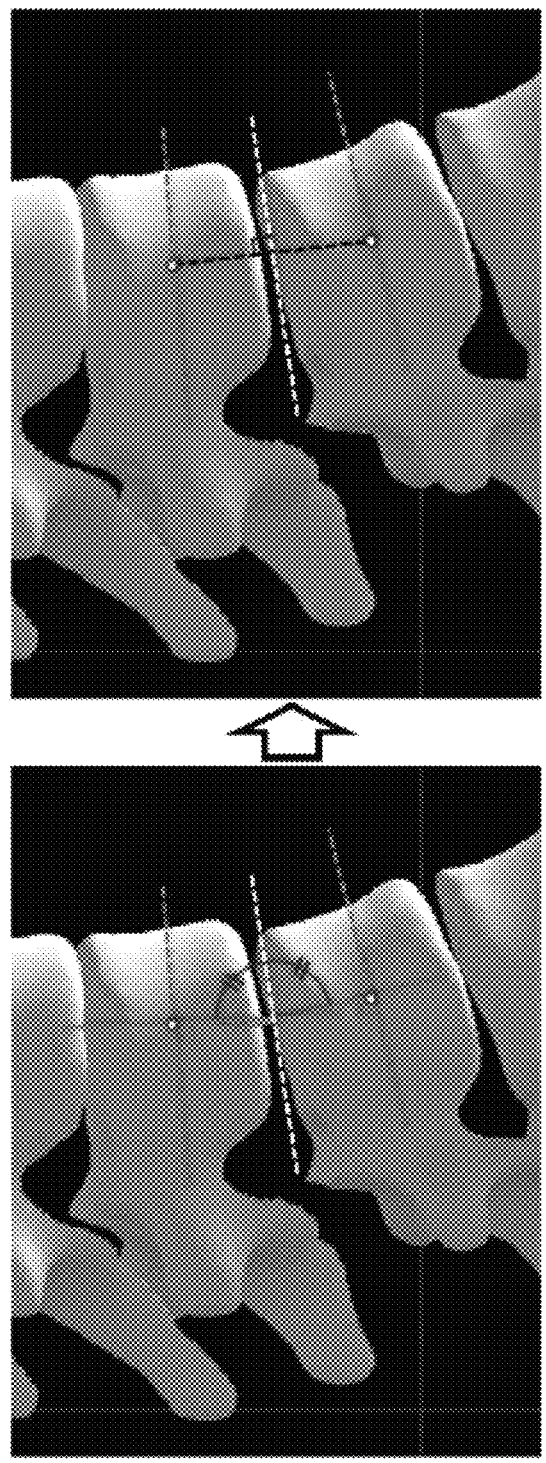
FIG. 9 illustrates a concept of generating the chain line using inclinations of upper and lower planes of two adjacent vertebral bodies according to an exemplary embodiment of the present disclosure.

FIG. 9 illustrates a concept of generating the chain line using inclinations of the upper and lower planes of two adjacent vertebral bodies according to an exemplary embodiment of the present disclosure.

That is, FIG. 9 shows an example in which the chain line is generated by using the inclinations of the upper and lower planes of two adjacent vertebral bodies, and a depth value of each vertebral body is calculated using chain line.

The calculation of the chain line connecting the vertebral bodies can be performed as follows.

In order to obtain a chain line using normal lines of the 3D planes of the vertebral bodies, the x-axis (horizontal) direction and the y-axis (vertical) direction in the front view as well as the z-axis (depth) direction are considered.

The x-axis and the y-axis in the front view are calculated by connecting centers of each vertebral body based on the front view image. The z-axis in the depth direction may be determined by using a line passing through central points of the two adjacent vertebral bodies along a direction vector which is an average vector of normal vectors of two planes when the y-axis is set vertically and the z-axis is set to indicate the depth. As a result, a relative depth, z-value, with respect to a reference can be calculated when one of the vertebral bodies is used as the reference. Finding the line as above may bring about an identical result as calculating a line passing through the central points of the adjacent vertebral bodies along a direction vector which is a normal vector of a plane bisecting an angle formed by the two normal vectors of the planes of the adjacent vertebral bodies when viewed in a direction perpendicular to a z-y plane.

Figure 10:
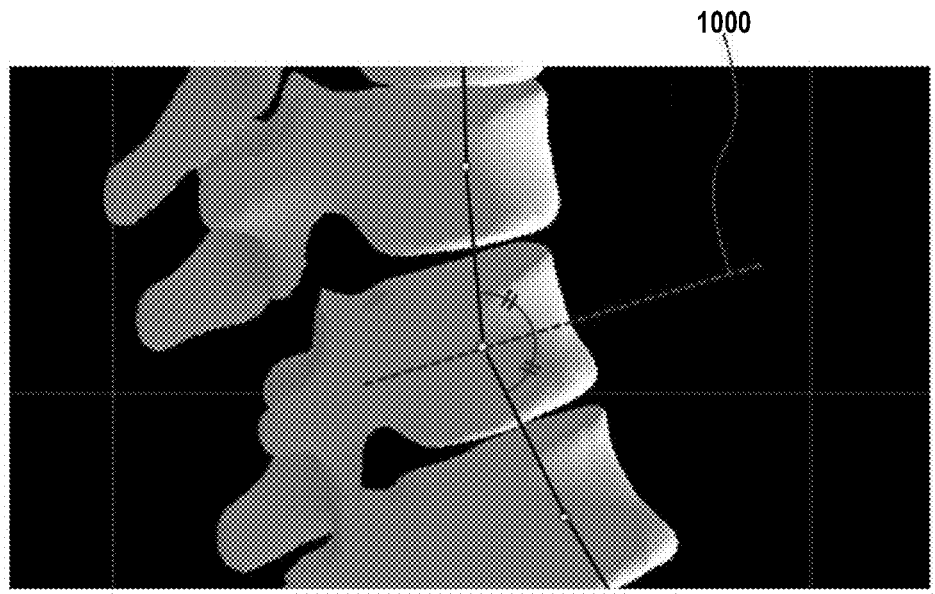
FIG. 10 illustrates a concept of a fine adjustment of a tilt of the vertebral body using an angle of the chain line connecting the vertebral bodies according to an exemplary embodiment of the present disclosure.

FIG. 10 illustrates a concept of a fine adjustment of a tilt of the vertebral body using an angle of the chain line connecting the vertebral bodies according to an exemplary embodiment of the present disclosure.

As described above regarding the exemplary embodiments, once the chain lines between the adjacent vertebral bodies are determined, relative depth values between all the vertebral bodies can be known with respect to one of the vertebral bodies, and the 3D model of the entire vertebrae in a 3D space described by a Cartesian coordinate system, for example, can be obtained. When the chain line connecting the vertebral bodies is calculated in such a manner, the direction of each vertebral body can be adjusted again by using the chain line.

The 3D vertebral body model generated by using the contour of a candidate for the 3D vertebral body model and the contour matching of the vertebral body in the X-ray image may be error-prone due to a contour estimation error or a 3D model matching error. Such an error may cause an error in the estimated plane. In order to correct this, the chain line connecting the vertebral bodies is used.

For the fine adjustment of each vertebral body, a reference plane is set in advance. The chain lines connected to vertebral bodies adjacent to the bottom and top of a certain vertebral body are regarded as direction vectors, and a plane using an average of the two direction vectors as a normal vector is determined as the reference plane 1000. This reference plane 100 bisects the angle formed by the two chain lines.

During the fine adjustment, the differences between the angles between the reference plane and the lower and upper planes of the vertebral body are adjusted using a weight. In case that the weight is large, the inclination values of the lower and upper planes are adjusted a lot so that the planes are as close to the reference plane as possible. In case that the weight is small, degrees of adjusting the inclination values of the lower and upper planes to the reference plane are reduced.

Figure 11:
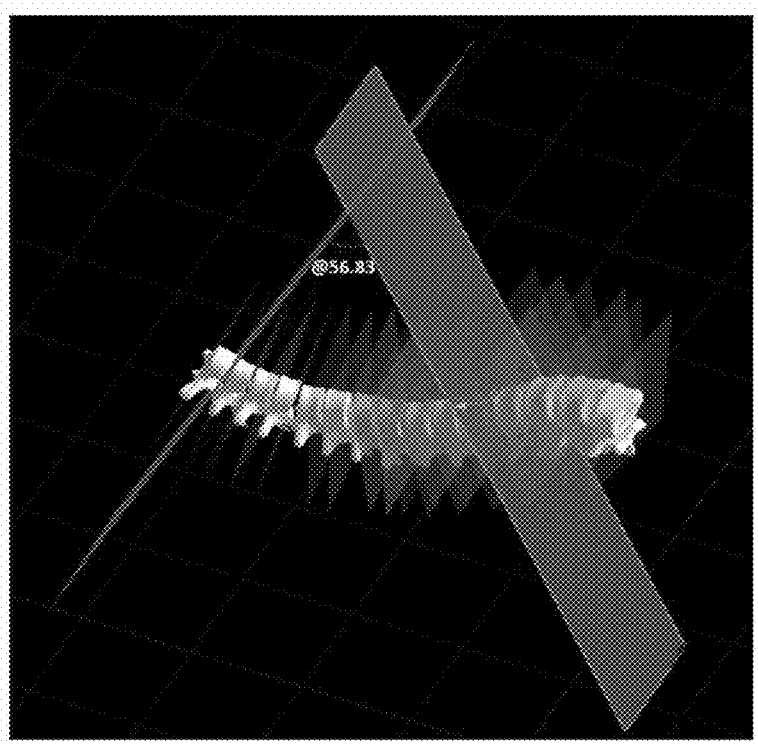
FIG. 11 illustrates a concept of analyzing a 3D Cobb's angle using the upper and lower planes of the vertebral body according to an exemplary embodiment of the present disclosure.

FIG. 11 illustrates a concept of analyzing a 3D Cobb's angle using the upper and lower planes of the vertebral body according to an exemplary embodiment of the present disclosure.

Since the planes of the vertebral bodies that have undergone the fine adjustment have directions having been adjusted in consideration of correlations between the adjacent vertebral bodies, it is possible to calculate the angle more stably. Two planes with a largest angle between the lower and upper planes of the vertebral bodies are selected in the 3D space, and the angle value between the two selected planes is determined as the 3D Cobb's angle.

In general, scoliosis is diagnosed in many cases by using a 2D Cobb's angle obtained from the frontal X-ray image. The present disclosure enables to obtain the 3D Cobb's angle using only the frontal X-ray image. The 3D Cobb's angle is calculated in consideration of the tilt in the side view as well as the tilt in the front view, and is generally larger by 10 degrees or more than an angle value obtained from the front view.

Since the human spine basically has a three-dimensional structure in the 3D space, it is desirable to reconstruct the spine three-dimensionally as in the present disclosure rather than analyzing in the 2D to use in the diagnosis of spinal diseases while maintaining the characteristics of the original spine model.

Figure 12:
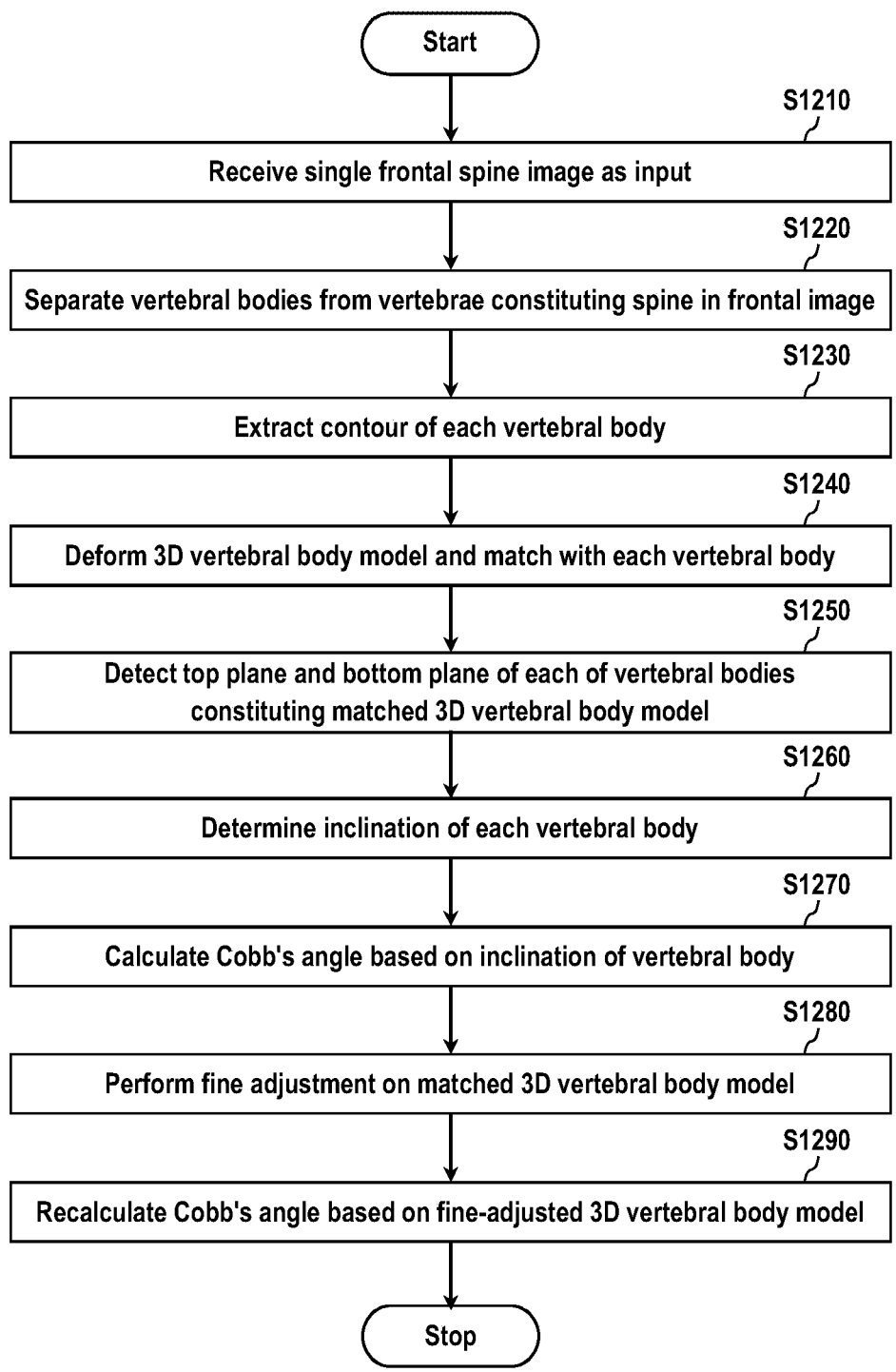
FIG. 12 is a flowchart showing a medical image analysis method according to an exemplary embodiment of the present disclosure.

FIG. 12 is a flowchart showing a medical image analysis method according to an exemplary embodiment of the present disclosure.

Referring to FIG. 12, when the medical image analysis apparatus according to the present disclosure receives a single frontal image of the spine as an input (S1210), the vertebral bodies are separated from the vertebrae constituting the spine in the frontal image (S1220) and the contour of each vertebral body is extracted (S1230). The frontal image received by the medical image analysis apparatus according to the present disclosure may be a 2D X-ray image.

Afterwards, the medical image analysis apparatus performs operations of deforming the 3D vertebral body model stored already and matching with the contour of each vertebral body (S1240). Here, the 3D vertebral body model can be deformed in its position, direction, and shape. Thus, the 3D vertebral body model may be matched with the contour of the vertebral bodies by changing at least one of the position, the rotation, and the shape of the 3D vertebral body model.

In the matching operation S1240, it is also possible to determine the forward tilt and the backward tilt of a certain vertebral body in consideration of the position of the certain vertebral body in the entire spine and the characteristics of the spine. The characteristics of the spine may include the features of the thoracic kyphosis and the lumbar lordosis, and the continuity between adjacent vertebral bodies.

After the matching is completed, the top plane and the bottom plane of each of the vertebral bodies constituting the 3D vertebral body model are detected (S1250), and the inclination of the vertebral body is determined based on the top plane and the bottom plane of the vertebral body (S1260). When the inclination of the vertebral body is determined, the Cobb's angle may be calculated based on the inclination of the vertebral body (S1270). Although it is shown in FIG. 12, for convenience of illustration, that the determination of the inclination of the vertebral body and the calculation of the Cobb's angle are performed after the operation of matching the 3D vertebral body model with the contour of the vertebral body, such operations may be performed after the fine adjustment of the 3D vertebral body model is completed.

In other words, the medical image analysis method according to the present disclosure may include operations of: performing the fine adjustment on the matched 3D vertebral body model (S1280), and calculating or recalculating the Cobb's angle based on the 3D vertebral body model having undergone the fine adjustment (S1290).

In the fine adjustment operation S1280 for the 3D vertebral body model, a chain line connecting the vertebral bodies constituting the spine may be set using the inclinations of the upper and lower planes of each vertebral body, a reference plane may be determined with reference to the chain line, and a difference in angles between the upper plane of a corresponding vertebral body and the reference plane and between the lower plane of the corresponding vertebral body and the reference plane.

The reference plane may be a plane of which normal vector is an average of two direction vectors that are parallel with chain lines connecting to a lower adjacent vertebral body and an upper adjacent vertebral body, respectively, of a certain vertebral body.

Also, the reference plane may be a plane bisecting the angle formed by a first chain line connecting to the lower adjacent vertebral body of the certain vertebral body and a second chain line connecting to the upper adjacent vertebral body of the certain vertebral body.

The Cobb's angle may be set as an angle between two arbitrary planes having a largest angle among the angles formed by any two of the upper planes and the lower planes of the vertebral bodies constituting the spine in the 3D space.

Although not shown in FIG. 12, the Cobb's angle calculated as above may be provided to diagnose spine-related diseases.

Figure 13:
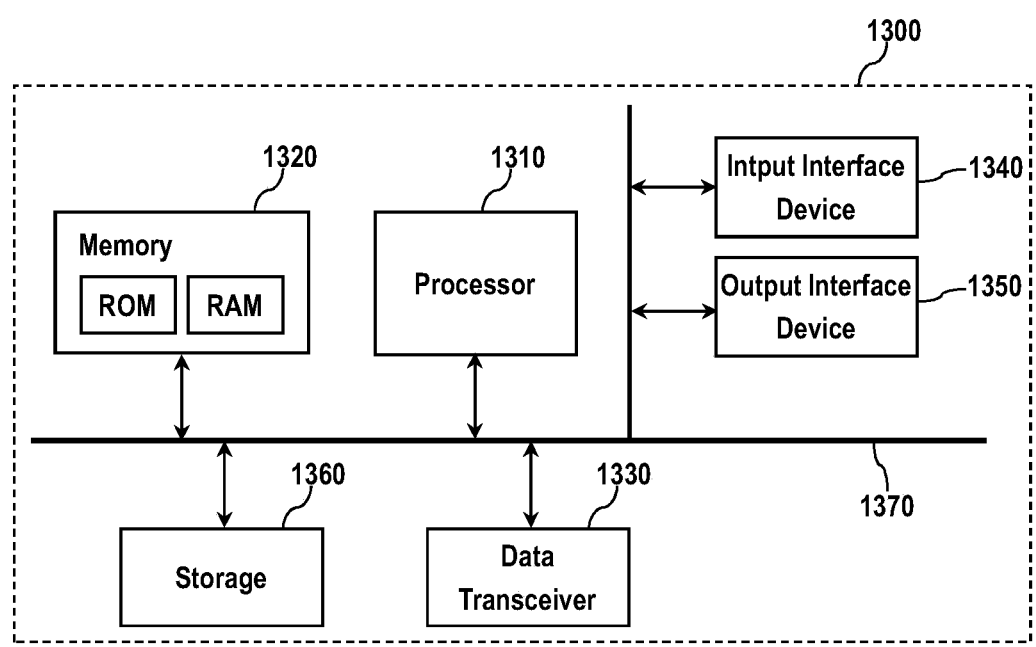
FIG. 13 is a block diagram of a medical image analysis apparatus according to another exemplary embodiment of the present disclosure.

FIG. 13 is a block diagram of the medical image analysis apparatus according to another exemplary embodiment of the present disclosure.

The medical image analysis apparatus 1300 according to the present embodiment may include at least one processor 1310, a memory 1320 for storing at least one instruction to be executed by the processor 1310, and a data transceiver 1330 performing communications through a network. The medical image analysis apparatus 1300 may further include an input interface device 1340, an output interface device 1350, and a storage device 1360. The components of the medical image analysis apparatus 1300 may be connected through a bus 1370 to communicate with each other.

The processor 1310 may execute program instructions stored in the memory 1320 and/or the storage 1360. The processor 1310 may include a central processing unit (CPU) or a graphics processing unit (GPU), or may be implemented by another kind of dedicated processor suitable for performing the methods of the present disclosure.

The memory 1320 may load the program instructions stored in the storage 1360 to provide to the processor 1310. The memory 1320 may include, for example, a volatile memory such as a read only memory (ROM) and a non-volatile memory such as a random access memory (RAM).

The storage 1360 may store the program instructions that can be loaded to the memory 1320 and executed by the processor 1310. The storage 1360 may include an intangible recording medium suitable for storing the program instructions, data files, data structures, and a combination thereof. Examples of the storage medium may include magnetic media such as a hard disk, a floppy disk, and a magnetic tape, optical media such as a compact disk read only memory (CD-ROM) and a digital video disk (DVD), magneto-optical medium such as a floptical disk, and semiconductor memories such as ROM, RAM, a flash memory, and a solid-state drive (SSD).

The program instructions, when executed by the processor, may cause the processor to: receive a frontal image of a spine and separate vertebral bodies from a vertebrae constituting the spine in the frontal image; extract a contour of each of the vertebral bodies; deform a 3D vertebral body model prepared in advance to match with the contour of each vertebral body; detect an upper plane and a lower plane of each vertebral body in a matched 3D vertebral body model; determine an inclination of each vertebral body based on the upper plane and the lower plane of each vertebral body; and calculate a Cobb's angle based on the inclination of the vertebral body.

The program instructions, when executed by the processor, may further cause the processor to: perform a fine adjustment of the 3D vertebral body model; and recalculate the Cobb's angle based on a fine-adjusted 3D vertebral body model.

The instruction causing the processor to deform the 3D vertebral body model to match with the contour of each vertebral body may include instructions causing the processor to: deform the 3D vertebral body model by changing at least one of a position, rotation, and shape of the 3D vertebral body model and match a deformed 3D vertebral body model with the contour of each vertebral body.

The instruction causing the processor to deform the 3D vertebral body model to match with the contour of each vertebral body may include instructions causing the processor to: determine a forward tilt or a backward tilt of a particular vertebral body in consideration of a position of the particular vertebral body in an entire body of the spine and characteristics of the spine.

The instruction causing the processor to perform the fine adjustment of the 3D vertebral body model may include instructions causing the processor to: set a chain line connecting the vertebral bodies constituting the spine using inclinations of the upper and lower planes of each vertebral body; determine a reference plane with reference to the chain line; and adjust a difference in angles between the upper plane of a corresponding vertebral body and the reference plane and between the lower plane of the corresponding vertebral body and the reference plane.

The reference plane may be a plane of which normal vector is an average of two direction vectors that are parallel with chain lines connecting to a lower adjacent vertebral body and an upper adjacent vertebral body, respectively, of a particular vertebral body.

The Cobb's angle may be set as an angle between two arbitrary planes having a largest angle among the angles formed by any two of upper planes and lower planes of the vertebral bodies constituting the spine in a 3D space.

The program instructions, when executed by the processor, may further cause the processor to: provide the Cobb's angle to diagnose a spine-related disease.

The image may be a 2D X-ray image.

As mentioned above, the apparatus and method according to exemplary embodiments of the present disclosure can be implemented by computer-readable program codes or instructions stored on a computer-readable intangible recording medium. The computer-readable recording medium includes all types of recording device storing data which can be read by a computer system. The computer-readable recording medium may be distributed over computer systems connected through a network so that the computer-readable program or codes may be stored and executed in a distributed manner.

The computer-readable recording medium may include a hardware device specially configured to store and execute program instructions, such as a ROM, RAM, and flash memory. The program instructions may include not only machine language codes generated by a compiler, but also high-level language codes executable by a computer using an interpreter or the like.

Some aspects of the present disclosure described above in the context of the apparatus may indicate corresponding descriptions of the method according to the present disclosure, and the blocks or devices may correspond to operations of the method or features of the operations. Similarly, some aspects described in the context of the method may be expressed by features of blocks, items, or devices corresponding thereto. Some or all of the operations of the method may be performed by use of a hardware device such as a microprocessor, a programmable computer, or electronic circuits, for example. In some exemplary embodiments, one or more of the most important operations of the method may be performed by such a device.

In some exemplary embodiments, a programmable logic device such as a field-programmable gate array may be used to perform some or all of the functions of the methods described herein. The field-programmable gate array may be operated along with a microprocessor to perform one of the methods described herein. In general, the methods may be performed preferably by a certain hardware device.

While the present disclosure has been described above with respect to exemplary embodiments thereof, it will be apparent to those skilled in the art that various changes and modifications may be made without departing from the spirit and scope of the present disclosure defined in the following claims.

What is claimed is:

1. A medical image analysis method, comprising:
receiving a frontal image of a spine;
separating vertebral bodies from a vertebrae constituting the spine in the frontal image and extracting a contour of each of the vertebral bodies;
deforming a 3D vertebral body model prepared in advance to match with the contour of each vertebral body;
detecting an upper plane and a lower plane of each vertebral body in a matched 3D vertebral body model;
determining an inclination of each vertebral body based on the upper plane and the lower plane of each vertebral body; and
calculating a Cobb's angle based on the inclination of the vertebral body.

2. The medical image analysis method of claim 1, comprising:
performing a fine adjustment of the 3D vertebral body model; and
recalculating the Cobb's angle based on a fine-adjusted 3D vertebral body model.

3. The medical image analysis method of claim 2, wherein performing the fine adjustment of the 3D vertebral body model comprises:
setting a chain line connecting the vertebral bodies constituting the spine using inclinations of the upper and lower planes of each vertebral body;
determining a reference plane with reference to the chain line; and
adjusting a difference in angles between the upper plane of a corresponding vertebral body and the reference plane and between the lower plane of the corresponding vertebral body and the reference plane.

4. The medical image analysis method of claim 3, wherein the reference plane is a plane of which normal vector is an average of two direction vectors that are parallel with chain lines connecting to a lower adjacent vertebral body and an upper adjacent vertebral body, respectively, of a particular vertebral body.

5. The medical image analysis method of claim 3, wherein the reference plane is a plane bisecting an angle formed by a first chain line connecting to a lower adjacent vertebral body of a particular vertebral body and a second chain line connecting to an upper adjacent vertebral body of the particular vertebral body.

6. The medical image analysis method of claim 1, wherein deforming the 3D vertebral body model to match with the contour of each vertebral body comprises:
deforming the 3D vertebral body model by changing at least one of a position, rotation, and shape of the 3D vertebral body model and matching a deformed 3D vertebral body model with the contour of each vertebral body.

7. The medical image analysis method of claim 1, wherein deforming the 3D vertebral body model to match with the contour of each vertebral body comprises:
determining a forward tilt or a backward tilt of a particular vertebral body in consideration of a position of the particular vertebral body in an entire body of the spine and characteristics of the spine.

8. The medical image analysis method of claim 7, wherein the characteristics of the spine comprises a feature of thoracic kyphosis or lumbar lordosis and a continuity between adjacent vertebral bodies.

9. The medical image analysis method of claim 1, wherein the Cobb's angle is set as an angle between two arbitrary planes having a largest angle among the angles formed by any two of upper planes and lower planes of the vertebral bodies constituting the spine in a 3D space.

10. The medical image analysis method of claim 1, further comprising:
providing the Cobb's angle to diagnose a spine-related disease.

11. The medical image analysis method of claim 1, wherein the image is a 2D X-ray image.

12. A medical image analysis apparatus, comprising:
a processor; and
a memory storing at least one instruction to be executed by the processor,
wherein the at least one instruction, when executed by the processor, causes the processor to:
receive a frontal image of a spine and separate vertebral bodies from a vertebrae constituting the spine in the frontal image;
extract a contour of each of the vertebral bodies;
deform a 3D vertebral body model prepared in advance to match with the contour of each vertebral body;
detect an upper plane and a lower plane of each vertebral body in a matched 3D vertebral body model;
determine an inclination of each vertebral body based on the upper plane and the lower plane of each vertebral body; and
calculate a Cobb's angle based on the inclination of the vertebral body.

13. The medical image analysis apparatus of claim 12, wherein the at least one instruction, when executed by the processor, further causes the processor to:
perform a fine adjustment of the 3D vertebral body model; and
recalculate the Cobb's angle based on a fine-adjusted 3D vertebral body model.

14. The medical image analysis apparatus of claim 12, wherein the instruction causing the processor to deform the 3D vertebral body model to match with the contour of each vertebral body comprises instructions causing the processor to:
deform the 3D vertebral body model by changing at least one of a position, rotation, and shape of the 3D vertebral body model and match a deformed 3D vertebral body model with the contour of each vertebral body.

15. The medical image analysis apparatus of claim 12, wherein the instruction causing the processor to deform the 3D vertebral body model to match with the contour of each vertebral body comprises instructions causing the processor to:
  determine a forward tilt or a backward tilt of a particular vertebral body in consideration of a position of the particular vertebral body in an entire body of the spine and characteristics of the spine.

16. The medical image analysis apparatus of claim 12, wherein the instruction causing the processor to perform the fine adjustment of the 3D vertebral body model comprises instructions causing the processor to:
  set a chain line connecting the vertebral bodies constituting the spine using inclinations of the upper and lower planes of each vertebral body;
  determine a reference plane with reference to the chain line; and
  adjust a difference in angles between the upper plane of a corresponding vertebral body and the reference plane and between the lower plane of the corresponding vertebral body and the reference plane.

17. The medical image analysis apparatus of claim 16, wherein the reference plane is a plane of which normal vector is an average of two direction vectors that are parallel with chain lines connecting to a lower adjacent vertebral body and an upper adjacent vertebral body, respectively, of a particular vertebral body.

18. The medical image analysis apparatus of claim 12, wherein the Cobb's angle is set as an angle between two arbitrary planes having a largest angle among the angles formed by any two of upper planes and lower planes of the vertebral bodies constituting the spine in a 3D space.

19. The medical image analysis apparatus of claim 12, wherein the at least one instruction, when executed by the processor, further causes the processor to:
  provide the Cobb's angle to diagnose a spine-related disease.

20. The medical image analysis apparatus of claim 12, wherein the image is a 2D X-ray image.

* * * * *

UNITED STATES PATENT AND TRADEMARK OFFICE
CERTIFICATE OF CORRECTION

Page 1 of 1

PATENT NO.       : 11,928,815 B2
APPLICATION NO.  : 17/353071
DATED            : March 12, 2024
INVENTOR(S)      : Hang Kee Kim It is certified that error appears in the above-identified patent and that said Letters Patent is hereby corrected as shown below:

On the Title Page

Include the following foreign application priority data:
(30) Foreign Application Priority Data
June 22, 2020 (KR) 1020200075785

Signed and Sealed this
Twenty-fifth Day of June, 2024

Katherine Kelly Vidal
*Director of the United States Patent and Trademark Office*